US00PP27995P2

(12) United States Plant Patent
Sato et al.

(10) Patent No.: US PP27,995 P2
(45) Date of Patent: May 9, 2017

(54) **NEW GUINEA *IMPATIENS* PLANT NAMED 'SAKIMP044'**

(50) Latin Name: ***Impatiens* hybrid hort**
Varietal Denomination: SAKIMP044

(71) Applicant: Sakata Seed Corporation, Yokohama (JP)

(72) Inventors: Chihiro Sato, Nagano (JP); Shinji Minemura, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 14/999,101

(22) Filed: Mar. 30, 2016

(51) Int. Cl.
*A01H 5/02* (2006.01)

(52) U.S. Cl.
USPC ..... Plt./318.6

(58) Field of Classification Search
USPC ..... Plt./318.6, 318.4
CPC ..... A01H 5/0261
See application file for complete search history.

*Primary Examiner* — Kent L Bell
(74) *Attorney, Agent, or Firm* — Barbara Campbell; Bethany R. Roahrig; Cochran Freund & Young, LLC

(57) ABSTRACT

An *impatiens* plant particularly distinguished by having red-purple flowers, a compact plant habit, and green leaves, is disclosed.

2 Drawing Sheets

Genus and species: *Impatiens* hybrid hort.
Variety denomination: 'SAKIMP044'.

BACKGROUND OF THE NEW PLANT

The present invention comprises a new and distinct variety of New Guinea *Impatiens* plant, botanically known as *Impatiens hybrida* hort, and referred to by the variety name 'SAKIMP044'. 'SAKIMP044' originated from an interspecific hybridization in Misato, Japan between the proprietary female breeding line 'NE-5331' (unpatented) having salmon-orange flowers and the proprietary male breeding line 'NI-549-37HB' (unpatented) having purple flowers and variegated leaves.

In May 2011, 'NE-5331' was crossed with 'NI-549-37HB' and a population of F1 plants were produced. The F1 plants were evaluated in Misato, Japan in an open field trial. The criteria for plant selection included deep flower color, compact growth habit, and strong root system. At the completion of the trial, a single plant was made based on the above criteria and vegetatively propagated and was designated 'M2014 260'. From June to August 2014, the selection was evaluated in an open field in Misato, Japan. Shoot-tip cuttings of the variety were then shipped to Salinas, Calif., where the plants were regenerated and re-evaluated for stability of traits. 'M2014 260' was subsequently named 'SAKIMP044'. 'SAKIMP044' was found to reproduce true to type in successive generations of asexual propagation via vegetative cuttings in Salinas, Calif.

SUMMARY

The following are the most outstanding and distinguishing characteristics of this new variety when grown under normal horticultural practices in Salinas, Calif.

1. Red-purple flowers and compact plant habit; and
2. Green leaves.

DESCRIPTION OF THE PHOTOGRAPHS

This *impatiens* plant is illustrated by the accompanying photographs which show the plant's overall plant habit including form, foliage, and flowers. The photographs are of a plant grown in Salinas, Calif. under greenhouse conditions. The colors shown are as true as can be reasonably obtained by conventional photographic procedures.

DESCRIPTION OF THE NEW VARIETY

Figure 1:
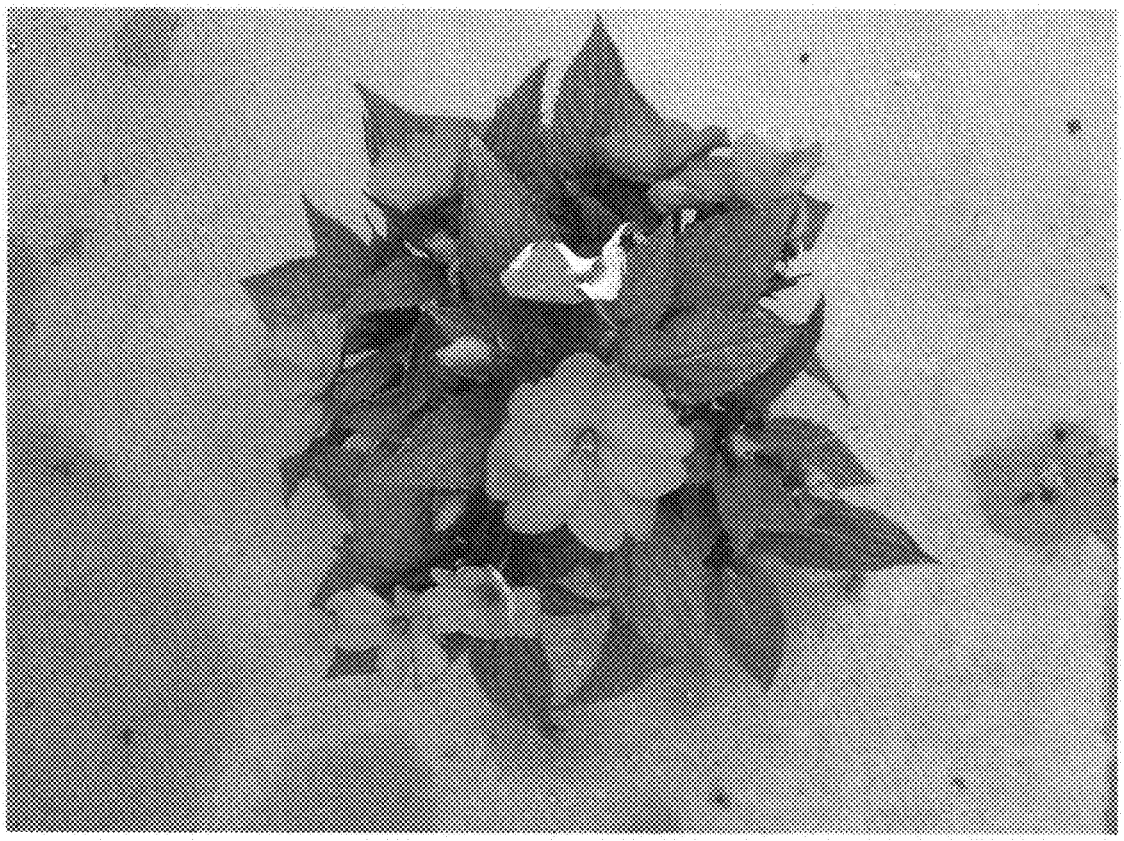
FIG. 1 shows the overall plant habit of the plant grown in a pot.
Figure 2:
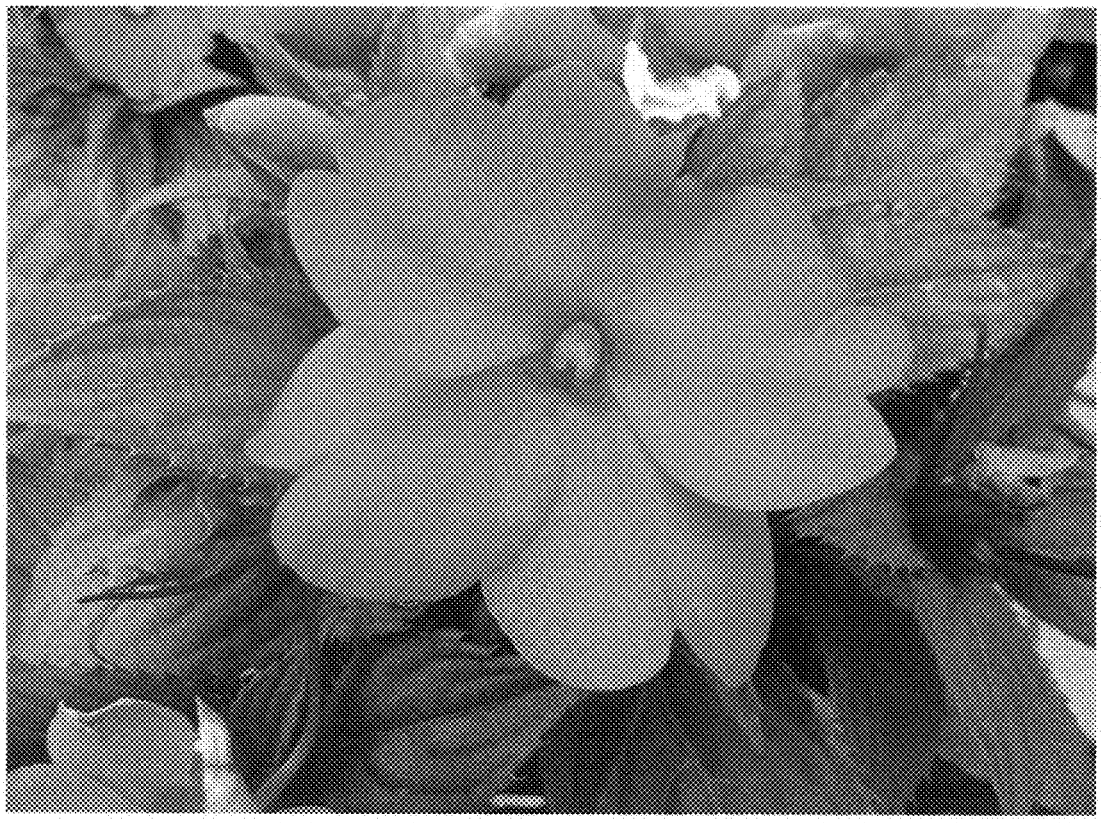
FIG. 2 shows a close-up of the mature inflorescence of the plant.

The following detailed descriptions set forth the distinctive characteristics of 'SAKIMP044'. Color references are to The Royal Horticultural Society of London color chart (R.H.S.), 4$^{th}$ edition (2001). Data was obtained from plants grown about 7-months from propagation by terminal cuttings in Salinas, Calif., under greenhouse conditions. Anatomic labels are from *The Cambridge Illustrated Glossary of Botanical Terms*, by M. Hickey and C. King, Cambridge University Press.

Classification:
*Family*.—Balsaminaceae.
*Botanical*.—*Impatiens hybrida* hort.
*Common*.—*Impatiens*.
*Designation*.—'SAKIMP044'.

Growth: Environmental conditions for plant growth: The terminal 1.0 to 1.5 inches of an actively growing stem was excised. The vegetative cuttings were propagated for five to six weeks. The base of the cuttings were dipped for 1 to 2 seconds in a 1:9 solution of DIP 'N GROW (1 solution:9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2-3 days, 2 times in consecutive applications and then given one clear water application. Pots were top-dressed with a dry, slow release fertilizer containing 20% nitrogen, 10% phosphorus and 18% potassium. The typical average air temperature was 24° C.

Parentage:

*Female parent*.—Proprietary *Impatiens* breeding line 'NE-5331'.

*Male parent*.—Proprietary *Impatiens* breeding line 'NI-549-37HB'.

Plant description:

*Life cycle*.—Annual.

*Habit*.—Compact.

*Height*.—27.0 cm from soil line to top of foliage.

*Spread*.—60.0 cm.

*Number of branches*.—34 total with 7 main branches.

*Length of branches*.—1.0 cm from soil line to first node, 8.0 cm to 10.0 cm total.

*Diameter of branches*.—2.0 cm for the main branch, 0.5 cm to 1.0 cm for other secondary branches.

*Color of branches*.—RHS 186C (Greyed-Purple).

*Time to produce a rooted cutting*.—About 4 weeks.

*Time to bloom from propagation*.—6 to 8 weeks.

*Flowering requirements* (*season*).—Will flower so long as temperature is above 5° C.

*Disease or pest resistance/susceptibility*.—No particular resistance or susceptibility observed.

*Temperature tolerances*.—Plants observed to continue flowering in a temperature range of 5° C. to 36° C.

Stems:

*Stem color*.—RHS 187B (Greyed-Purple).

*Anthocyanin color*.—RHS 18B (Greyed-Purple).

*Stem pubescence*.—None.

*Stem description*.—Strong; circular cross-section, smooth and shiny.

*Stem length*.—10.0 cm from first to second node, 16.0 cm total.

*Stem diameter*.—6.0 mm.

*Internode length*.—10.0 cm, 5.0 cm to 9.0 cm from first to second node.

Leaves:

*Leaf arrangement*.—Whorled with up to 5 leaves per node, opposite if only two leaves at one node.

*Leaf shape*.—Lanceolate, curled.

*Leaf tip*.—Acuminate.

*Leaf base*.—Shortly attenuate.

*Leaf margin*.—Serrate.

*Leaf surface*.—Dull; waxy.

*Leaf length*.—9.3 cm.

*Leaf width*.—3.3 cm.

*Leaf color*.—Upper: closest to but darker than RHS 147A (Yellow-Green). Lower: RHS 147B (Yellow-Green).

*Leaf variegation*.—Absent.

*Leaf fragrance*.—Absent.

*Leaf surface pubescence*.—Absent.

*Petiole length*.—1.0 cm.

*Petiole diameter*.—3.0 mm.

*Petiole color*.—RHS 59A (Red-Purple).

*Petiole texture*.—Smooth, glabrous.

*Venation*.—Pinnate. Upper vein color: Closest to RHS 145 D (Yellow-Green). Lower vein color: Closest to RHS 59A (Red-Purple).

Flowers:

*Number of flowers per node*.—1 to 3 in bloom at one time; about 10 flower buds.

*Number of flowers per plant*.—Approximately 100 in bloom.

*Lastingness of individual blooms on the plant*.—14 days.

*Inflorescence type*.—Single flower with spur.

*Fragrance*.—Absent.

*Corolla*.—Corolla shape: Roughly circular with 5 radial petals. Corolla diameter: 6.0 cm. Corolla depth: 1.5 cm.

*Calyx*.—Sepal Shape: Lanceolate. Sepal Number: 2. Sepal color: Upper surface: RHS 58 (Red-Purple) with slight RHS 144 (Yellow-Green) at the tip. Lower surface: RHS 46D (Red) with RHS 143A (Green) at the tip. Sepal Length: 1.2 cm. Sepal diameter: 7.0 mm. Sepal Base: Subcordate. Sepal Apex: Caudate. Sepal Margin: Entire. Sepal texture: Glabrous.

Petals:

*Corolla shape*.—Roughly circular with 5 radial petals.

*Petal pubescence*.—Glabrous.

*Petal length*.—2.8 cm.

*Petal width*.—3.0 cm.

*Petal shape*.—Obcordate.

*Petal apex*.—Emarginate (cleaved).

*Petal margin*.—Entire.

*Petal base*.—Attenuate.

*Petal color*.—Upper surface: Closest to but darker than RHS N74A (Red-Purple). Lower surface: RHS N74A (Red-Purple). Eye zone: RHS 71A (Red-Purple).

Spur:

*Spur color*.—RHS 60A (Red-Purple) with RHS N77A (Purple) at the tip.

*Spur shape*.—Tubular; curved downward.

*Spur length*.—6.8 cm.

*Spur diameter*.—1.0 mm to 2.0 mm.

Bud:

*Bud surface*.—Glabrous.

*Bud length*.—1.5 cm.

*Bud diameter*.—1.0 cm.

*Bud shape*.—Deltoid longitudinal cross-section.

*Bud color*.—RHS 71 (Red-Purple).

Reproductive organs:

*Stamens*.—Stamen form: Fused; split into 4 lobes. Stamen number: Many. Filament length: 5.0 mm. Filament color: RHS 144C (Yellow-Green). Anther length: 7.0 mm. Anther color: Closest to RHS 59 A (Red-Purple).

*Pistil*.—Pistil number: 5. Stigma color: Upper part is RHS 187A (Greyed-Purple) and lower part is RHS 144C (Yellow-Green). Style color: RHS 144C (Yellow-Green). Ovary arrangement: Parietal. Ovary surface color: Closest to 149A (Yellow-Green). Pollen number: Abundant. Pollen color: RHS 155A (White). Pollen description: Powdery. Seed production: Not observed.

COMPARISON WITH PARENTAL AND COMMERCIAL VARIETIES

'SAKIMP044' is a new and unique variety of *Impatiens* owing to its compact growth habit, deep Red-purple flower color, and strong root system. 'SAKIMP044' is distinguished from its parents as shown in Table 1 below:

TABLE 1

Comparison with Parental Lines

| Characteristic | 'SAKIMP044' | Female Parent 'NE-5331' | Male Parent 'NI-549-37HB' |
|---|---|---|---|
| Flower color | Red-purple | Salmon-orange | Purple |
| Leaf variegation | Absent | Absent | Present |

'SAKIMP044' is a new and unique variety of *Impatiens* owing to its compact growth habit, deep Red-purple flower color, and strong root system. When 'SAKIMP044' compared to the commercial *Impatiens* variety 'SAKIMP029' (U.S. Plant Pat. No. 26,692), the following differences as described in Table 2 below.

TABLE 2

Comparison with Similar Variety

| Characteristic | 'SAKIMP044' | 'SAKIMP029' |
|---|---|---|
| Petal color, upper surface | Closest to but darker than RHS N74A (Red-purple) | RHS N74A (Red-purple) |
| Spur color | RHS 60A (Red-purple) with RHS N77A (Purple) at the tip | RHS 61A (Red-purple) |
| Venation color, upper vein color | Closest to RHS 145D (Yellow-green) | RHS 59A (Red-purple) |

We claim:

1. A new and distinct variety of New Guinea *impatiens* plant named 'SAKIMP044' as described and illustrated herein.

* * * * *